United States Patent [19]

Ward, Jr. et al.

[11] Patent Number: 4,686,137
[45] Date of Patent: Aug. 11, 1987

[54] MOISTURE VAPOR PERMEABLE MATERIALS

[75] Inventors: Robert S. Ward, Jr., Lafayette; Judy S. Riffle, Oakland, both of Calif.

[73] Assignee: Thoratec Laboratories Corp., Berkeley, Calif.

[21] Appl. No.: 612,365

[22] Filed: May 21, 1984

Related U.S. Application Data

[63] Continuation-in-part of Ser. No. 507,517, Jun. 24, 1983, which is a continuation-in-part of Ser. No. 385,813, Jun. 7, 1982, abandoned, and a continuation-in-part of Ser. No. 472,189, Mar. 4, 1983, abandoned, which is a continuation-in-part of Ser. No. 385,813, which is a continuation of Ser. No. 278,664, Jun. 29, 1981, abandoned, which is a continuation of Ser. No. 125,845, Feb. 29, 1980, abandoned.

[51] Int. Cl.$^4$ .............................................. B32B 27/00
[52] U.S. Cl. .................................... 428/290; 428/423.1; 525/403; 525/410; 525/453; 528/28; 528/76
[58] Field of Search ................ 525/403, 453, 410; 428/423.1, 290; 528/28, 76

[56] References Cited

U.S. PATENT DOCUMENTS

| 3,425,999 | 2/1969 | Axelrood et al. | 528/76 |
| 3,541,053 | 11/1970 | Harrell | 525/453 |
| 3,567,499 | 3/1971 | Klebert et al. | 525/453 |
| 3,666,542 | 5/1972 | Kigane et al. | 525/403 |
| 4,120,850 | 10/1978 | Pechhold | 525/410 |
| 4,124,572 | 11/1978 | Mao | 528/76 |
| 4,190,566 | 2/1980 | Noll et al. | 528/76 |
| 4,224,432 | 9/1980 | Pechhold et al. | 528/76 |
| 4,367,327 | 1/1983 | Holker et al. | 528/76 |
| 4,464,431 | 8/1984 | Hisaki et al. | 525/453 |

FOREIGN PATENT DOCUMENTS 711761 6/1965 Canada .............................. 528/28

*Primary Examiner*—Wilbert J. Briggs, Sr.
*Attorney, Agent, or Firm*—Flehr, Hohbach, Test, Albritton & Herbert

[57] ABSTRACT

Polymeric materials are provided characterized by hard segments and copolymer soft blocks comprising hydrophobic and hydrophilic components. The polymeric materials may be mixed with a base polymer and/or inorganic salts. The polymeric materials and mixtures containing same are characterized by improved moisture vapor transmission rates. The polymeric materials may be formed into films for use as wound dressings, burn dressings, surgical drapes, semipermeable membranes, and coatings for textiles.

6 Claims, 6 Drawing Figures

MOISTURE VAPOR PERMEABLE MATERIALS

This application is a continuation-in-part of co-pending Ser. No. 507,517, filed June 24, 1983, which in turn is a continuation-in-part of Ser. No. 385,813, filed June 7, 1982, now abandoned, and a continuation-in-part of co-pending Ser. No. 472,189, filed Mar. 4, 1983, now abandoned, the latter of which is a continuation-in-part of Ser. No. 385,813, filed June 7, 1982, which in turn is a continuation of Ser. No. 278,664, filed June 29, 1981, now abandoned, which is a continuation of Ser. No. 125,845, filed Feb. 29, 1980, now abandoned.

The present invention is directed to moisture vapor premeable materials. These materials are segmented block multipolymers and may be used alone or in a mixture with a base polymer. Such materials are useful as membranes, wound dressing, surgical drapes and burn dressings and as coatings for fabrics for apparel and industrial used.

Moisture vapor permeable backing materials having a moisture vapor permeable pressure sensitive adhesive are disclosed by Hodgson in U.S. Pat. No. 3,645,835. The backing materials disclosed therein are synthetic polymers which are continuous and nonpermeable to liquid water. The adhesive materials are also permeable to moisture vapor. There is no disclosure of a discrete segmented block copolymer additive to either the backing material polymer or the adhesive material polymer to increse the moisture vapor transmission capability. Other materials have been suggested for use as additives to polymers used in bio-medical devices, however, not for the purpose of enhancing moisture vapor transmission. For example, Nyilas in U.S. Pat. No. 3,562,352 suggests cross-linked thermosetting polysiloxane-polyurethane block copolymers for use as blood contact surfaces of bio-medical devices. The technique disclosed therein includes fabricating the entire blood contacting device from such block copolymers or coating such devices with the copolymers.

Minor amounts of block copolymers including segments of polydimethylsiloxane and blocks of polycarbonate, polystryrene, poly-(2,6-diphenyl-1,4-phenyleneoxide), and polyaide-imide have been blended with base homopolymers for modifying the surface properties of the homopolymers. Gaines, et al. in U.S. Pat. No. 3,961,122 suggest using such surface modified polymers as thin films while Gaines, et al. in U.S. Pat. No. 3,686,355 suggest a variety of uses, including bulk uses.

Flexible, soil resistant sheet material comprising a fibrous mat covered with a polyurethane composition is disclosed in U.S. Pat. No. 4,233,359. The polyurethane composition contains 0.1 to 5% of a surface active agent comprising a polyethylene oxide hydrophilic component and a hydrophobic component selected from polyalkylene oxides (except polyethylene oxides), aliphatic polyesters and mixtures thereof. No hydrophobic soft blocks such as polydialkylsiloxanes, are disclosed as part of the surface active agent.

Block copolymers useful in the treatment of fibrous materials to improve soil release properties are disclosed in U.S. Pat. No. 3,565,845. The block copolymers are not mixed with a base polymer when used to treat the fibrous materials. When applying dressing materials to wounds on the body, it is desired to utilize a material which is not permeable to liquid water in order to keep the wound from external contact with liquids, dirt and other particles. Additionally, the liquid water impermeability is desirable in order to minimize or eliminate transepidermal water loss from the body through the wound. On the other hand, to facilitate healing and to avoid maceration of the skin surrounding the wound it is necessary that moisture formed at the wound site be removed to a great extent. Therefore, this moisture may be removed by moisture vapor transmission through the wound dressing.

It is thus desirable to have a material as a wound dressing which is both impermeable to liquid water but yet highly permeable to water vapor, while still retaining structural integrity sufficient for the wound dressing, such as having high tear strength, flexibility, elongation (so that the material may be stretched over joints and limbs to conform to contours of the body) and high tear propagation so that cuts intentionally created in the material do not propagate across the dressing and cause failure.

In the textile industry, synthetic materials have been used to impart soil-releasing properties and waterproofing to fabrics. However, such materials suffer from the disadvantage of poor moisture vapor transmission. Thus prespiration tends to condense inside clothing made of such fabrics, making them uncomfortable particularly in hot or humid weather.

It would thus be desirable to provide textile materials which, in addition to having excellent tensile strength, elongation and impermeability to liquid water, also have a high permeability to water vapor.

It is therefore an object of the present invention to provide a wound dressing material having high moisture vapor transmission but being impermeable to liquid water.

It is a further object of the present invention to provide a segmented block copolymer additive compatible with numerous base polymers to form wound dressings, burn dressings, and surgical drapes having high moisture vapor transmission capability.

It is another object of the present invention to provide a segmented block copolymer which may be used alone or in a mixture with a base polymer to form coatings for textiles having high soil-release properties, high impermeability to liquid water, high textile strength and elongation, and high permeability to water vapor.

It is also an object of the present invention to provide a method for controlling the mositure vapor transmission properties of numerous base polymers by using segmented block copolymer additives.

These and other objects will become apparent from the following description of the preferred embodiments.

The present invention is directed to moisture vapor permeable materials comprising segmented block multipolymer which may be used alone or in a mixture with a base polymer. The block multipolymer comprises an essentially linear segmented copolymer chain characterized by at least one hard segment and at least one copolymer soft block comprising hydrophobic and hydrophilic components. The moisture vapor transmission materials according to the present invention are useful as burn dressings, wound dressings, surgical drapes, surgical sutures, and the like, and as coatings for apparel and industrial uses.

The materials according to the present invention will usually be formed by admixing a base polymer and a segmented block multipolymer additive in a solution and casting the admixture as a film. Removing the solvent by evaporative procedures will result in a material having a high moisture vapor capability.

When used without a base polymer, the block multipolymer will usually be dissolved in a solvent, then cast as a film or coating. This method is particularly preferred for forming moisture vapor permeable coatings on textiles.

As used herein, the term "base polymer" will refer to the polymer whose moisture vapor transmission characteristics are modified by the block multipolymer additive. Such base polymers may be segmented or block copolymers, blends thereof, thermoplastic homopolymers, or homopolymer mixtures which may also contain plasticizing agents. For example, plasticized polyvinylchloride and polyethylene may be used as base polymers.

Typical base polymers which may be utilized according to the present invention include polyurethanes, polysulfones, polyesters, polyethylenes, polypropylenes, polystyrenes, poly(acrylonitrile-butadiene-styrene), polybutadiene, polyisoprene, styrene-butadiene-styrene block copolymers, styrene-isoprent-styrene blockcopolymers, poly-(4-methylpentent), polyisobutylene, polymethylmethacrylate, polyvinylacetate, polyacrylonitrile, polyvinylchloride, polyethylene terephthalate, cellulose and its esters or derivatives, and the like.

The term "segmented" refers to the relatively short length of repeating units, e.g., less than about ten monomeric units, but preferably less than three monomeric units, typically alternating more than once, with structural formulas, such as ABAB.

A preferred class of base polymers includes the polyurethanes, including polyether urethane ureas, polyether urethanes and polyester urethanes. The polyrethanes or polyurethane ureas may be the reaction products of polymeric ether glycols and a diisocyanate, and a chain extending diamine or dihydroxy derivative. By the use of various types of isocyanates (e.g., aliphatic or aromatic), glycols (e.g., polyethylene, polypropylene, or polytetramethylene oxides), and chain extenders (aliphatic or aromatic), the structural properties of the base polymer may be varied depending upon the end use of the material.

A particularly preferred base polymer is a polyurethane urea formed from the polymerization of diphenylmethane diisocyanate (MDI), ethylene diamine (ED), and polytetramethylene oxide (PTMO).

Other base polymers include polyester-polyethers, polyesters (e.g., Dacron), polyether-polyamides, polyamides (e.g., nylon), styrene-isoprenes, styrene butadienes, thermoplastic polyolefins, styrene-saturated olefins, copolyesters, ethylene vinyl acetate, ethylene ethyl acrylate, ionomers, thermoplastic polydienes, and the like.

The segmented block multipolymers according to the present invention comprise an essentially linear segmented copolymer chain characterized by at least one hard segment and at least one copolymer soft block comprising hydrophobic and hydrophilic components. The block multipolymer may or may not be of the thermosetting type. The hard segment may be relatively short in length, typically including from one to ten repeating units. Preferably, the hard block will be a homopolymer wherein the hard segments comprise urethane selected from the same polymers which comprise the preferred polyurethane urea base polymers. When the segmented block multipolymer is used as an additive the similarity of the urethane segments of the additive and the urethane of the base polymer will cause the additive to be at least partially compatible with the base polymer in the admixture.

The copolymer soft block(s) of the block multipolymer may comprise both hydrophobic and hydrophilic components. The hydrophobic components of the soft block may be, for example, a tetraalkylene oxide or a polydialkylsiloxane. Techniques for forming siloxane copolymers are known, e.g., as described by Noll, *Chemistry and Technology of Silicones* (Academic Press, 1968), disclosure of which is incorporated by reference herein. Other suitable hydrophobic soft block components include polyfluoroalkyl alkylsiloxanes, polyfluoroalyl acrylates and methacrylates and copolymers thereof, polyolefins, polydienes, polyfluorocarbons, and the like.

The hydrophilic component of the soft block may be a polyalkylene oxide, polyvinylalkanoate (such as, polyvinyl acetate, polyvinylpropionate), and the like.

A preferred first class of compositions is one in which the soft blocks consist of both hydrophilic and hydrophobic components. The preferred hydrophilic component is polyethylene oxide (PEO) and the preferred hydrophobic component is polytetramethylene oxide (PTMO). The hard segments peferably comprise condensation products of diphenylmethand diisocyanate (MDI) with a diamine or diol. A particularly preferred hard segment will contain hard segments of MDI and ethylene diamine.

A preferred second class of compositions is one in which the soft blocks comprise hydrophilic nd hydrophobic components, preferably the PEO and PTMO components described above, and another hydrophobic component, preferably a polydialkylsioxane. The hard segments will be as described above, i.e., copolymers of MDI with a diamine or diol.

A particularly preferred composition of the first class will comprise the following:

| | |
|---|---|
| 15-50% | (by weight) hard segment |
| 20-45% | polyethylene oxide (1000-3000 mol. wt. (number avg.)) |
| 25-65% | polytetramethylene oxide |
| 0-2% | antiblocking/wetting agent, preferably a siloxane |

| -continued |
|---|
| 100% |

A particularly preferred composition of the second class comprises urethane hard segments (formed from MDI and butanediol) and soft blocks of siloxane (hydrophobic), polyethylene oxide (hydrophilic) and polytetramethylene oxide (hydrophobic).

In addition to the above block multipolymer, the moisture vaor permeable material according to the present invention may contain an inorganic salt, such as lithium bromide. Other inorganic salts may be used which are soluble in the casting solvent for the polyurethane urea. It is preferable that both the organic polymer and the inorganic salt be used in combination, since in many cases, the moisture vapor transmission rate of the base polymer will be enhanced by an unexpected amount.

The amounts of each of the block multipolymer additives which will be added to the base polymer, when used, will depend upon the base polymer and additives which are used. Generally, the organic polymer additive will be added in an amount to achieve a silicone (or other hydrophobic soft block component) concentration of at least 0.5% (by weight) in the admixture containing both base polymer and additive. The silicone (or other hydrophobic soft block component) content may vary between 0.1% and 50%. The inorganic salt additive, if ued, will generally be added in an amount to achieve a final concentration of about 0.5% (by weight) of the salt in the admixture containing the base polymer and all of the additives. The concentration of the inorganic salt may vary between 0.01% and 1.0%.

In the above concentration ranges, the additives according to the present invention will cause an increase of the moisture vapor transmission rate of the base polymer by about 10 to 500%, when cast in films ranging in thickness from 0.5 mil to 2.0 mil (1 mil=1/1000 inches=25.4001 microns).

To cast the films, the base polymer will normally be dissolved in an appropriate solvent, such as dimethylacetamyde (DMAC), dimethylformamide (DMF), toluene/isopropanol, tetrahydrofuran (THF), and the like. The additives will then be added and the film will be cast according to conventional procedures onto a support. Upon evaporation of the solvent a film will remain comprising materials according to the present invention. Similar methods may also be utilized to form thermoplastic films.

The base polymers utilized according to the present invention may be those conventionally known in the art, i.e. polyurethanes, polyetherurethaneureas, polyetherurethanes, polyesterurethanes, polyester/polyether, thermoplastic elastomers, and the like, many of which are commercially available as Estanes (B. F. Goodrich Company), Pellethane (Upjohn), Hytrel and Lycra Spandex (DuPont).

The segmented block multipolymers according to the present invention may be suitably formed of block copolymers of alternating hard segment and soft block components interlinked by chemical bond in accordance with the method set forth by Noshay and McGrath, *Block Copolymers Overview and Critical Survey* (Academic Press 1977), the disclosure of which is incorporated by reference herein. A suitable number of repeating units of each polymer of the hydrophobic and hydrophilic soft block components will typically be on the order of 1 to 100 units.

The procedure for preparation of the segmented block multipolymer additive may be performed by several procedures which differ in the degree to which the structure of the resultant product may be defined.

One procedure involves a coupling of two (or more) preformed blocks or segments which are prepared in separate reactions prior to the coupling reaction. This procedure involves a well defined structure if the coupling reaction precludes like blocks or segments from reacting with themselves, but only allows dissimilar blocks or segments to couple to one another.

Other coupling reactions may occur resulting in a less defined structure if the two performed blocks or segments possess the ability (via the coupling reaction) to react with themselves as well as the dissimilar block or segment.

Additional coupling reactions may occur when a single (or more) preformed block or segment is coupled with a second block or segment created during the coupling reaction. In this case the initial length of the performed block or segment is known, by virtue of their separate reaction used to prepare but the sequence of the distribution of the copolymer is not known exactly since both coupling and chain growth is possible in the reaction. Suitable methods of forming these and other such copolymers for use in the present invention are set forth in the aforementioned Noshay and McGrath publication.

A typical procedure is given below:

Charge the reactor with 9.75 g (0.015 moles) of a linear, difunctional, hydroxy terminated polytetramethylene oxide, 72 g (0.03 moles) of a linear, difunctional, hydroxy terminated polyethylene oxide/polydimethylsiloxane block copolymer, and 400 ml of a 1:1 (V/V) mixture of dimethylsulfoxide and methyl, isobutyl ketone. Heat the mixture to 75°–80° C. and add 37.5 g (0.15 moles) diphenylmethane diisocyanate (MDI) dissolved in 100 ml of a 1:1 (V/V) dimethylsulfoxide methyl, isobutyl ketone solvent mixture. Maintain the 75°–80° C. temperature with agitation and a dry nitrogen purge for three hours. Cool the reaction mixture to 45° C., then add 9.5 g (0.106 mole) butanediol in 200 ml of the 1:1 (V/V) dimethylsulfoxide/methyl, isobutyl ketone solvent. Maintain the 45° C. temperature for approximately 2 hours. Isolate the polymer via coagulation in water.

The above preferred additive will be used in the preferred base polymer, which is a low durometer polyurethaneurea based on diphenylmethane diisocyanate (MDI), ethylenediamine (ED) and polytetramethylene oxide (PTMO). A typical procedure is outlined below.

Charge a stirred, dry nitrogen purged reaction vessel with 8.60 g (0.034 moles) diphenylmethane diisocyanate, 50.0 g (0.025 moles) polytetramethylene oxide, and 100 ml anhydrous dimethylformamide at 45° C. Maintain the 45° C. temperature for 1 hour, 15 minutes. Remove the heat, dilute the mixture with 200 additional ml anhydrous dimethylformamide and add 0.54 g (0.009 moles) ethylene diamine incrementally over a 20 minute period.

Typically, the base polymer will be dissolved in the solvent, preferably dimethylacetamide, and the additives will be added to the solution based on the weight of the base polymer. The amount of solvent which is used will depend at least in part on the thickness of the desired film. The thicknesses of the films which are desired will depend upon the ultimate use to which the film will be utilized.

The compatibility between the base polymer and the organic polymer additive may be controlled by using a constant silicone soft segment and varying the chemistry of the remainder of the components of the admixture. Therefore, if the base polymer is Estane 5714, the additive may be a polymer containing a low molecular weight silicone with the remainder of the additive comprising MDI, butanediol, and PTMO. On the other hand, using the same silicone content in a copolymer or a polymer additive containing ethylene diamine, polybutylene adipate and MDI may give a different compatibility with the same Estane 5714 base polymer at equivalent concentrations. Therefore, the choice of the amounts and types of additives and base polymers which are utilized according to their present invention may be readily determined to achieve the most effective MVTR according to the teachings of the present invention.

In addition to the organic multipolymer additive and, if used, the inorganic salt additive, other additives may be utilized in the admixture depending upon the intended use of the film. For instance, if the films are to be utilized as burn wound dressings, it may be desirable to incorporate a water soluble leachable material. In this manner the higher the content of water soluble components, the higher the MVTR following dissolution of the leachable by the water produced by the wound. Furthermore, the water soluble leachable may be a carrier for an antimicrobial agent which will also serve to prevent or retard infection in the wound. Therefore, dissolution by the water in the wound and/or softening and flowing due to body heat will distribute the antimicrobial agent over the wound in a controlled release fashion. The antimicrobial agent may be mechanically mixed with the water soluble leachable material prior to addition to the film casting solution or may be chemically bonded to the water soluble leachable material.

Wound dressings according to the present invention may be made which have high elongation and excellent tear propagation so that the films may be stretched over joints and limbs to conform to parts of the body, while retaining the capability of being intentionally torn or cut without propagating rips across the dressing. A particularly preferable wound dressing material may comprise a polyether/polyester elastomer commercially available under the name Hytrel (Dupont) as the base polymer. Particularly preferred wound dressings may be formed utilizing a silicone containing block copolymer additive according to the present invention together with polyethyleneglycol, which is a water leachable component. For example, Hytrel 40D may be dissolved in methylene chloride with a thixotropic additive, such as Cab-O-Sil fume silica, to thicken the solution. Polyethyleneglycol may be added, which also increases the polarity of the system. This, in turn, increases the effectiveness of Cab-O-Sil as a thixotropic agent.

Textiles formed according to the present invention will have low permeability to liquid water, high permeability to water vapor, high tensile strength and elongation. Generally, fabrics will be coated with a composition comprising either a segmented block multipolymer or a mixture of a base polymer and block multipolymer additive by conventional coating techniques. The compositions according to the present invention are particularly advantageous as fabric coatings due to excellent adhesive properties, and lack of tackiness which allows the coated fabrics to be easily sewn. In addition, the viscosity of the bulk composition is in the range which permits easy handling for coating techniques. Finally, the coated fabrics have a pleasing texture and are more cloth-like in feel than conventional water impermeable synthetic materials which characteristically have broadly texture. While not intending to limit the invention by a particular theory, it is believed that commercially available water impermeable coated textiles are microporous while the coated textiles according to the present invention form a substantially solid sheet of water-vapor permeable material to give a pleasing cloth-like texture while improving the soil-release and liquid water impermeability. Coated fabrics according to the present invention are useful as rainwear, uphostery, shoe tops, tablecloths, tarpaulines, protective interliners for clothing proofed against chemical agents, and similar uses where liquid, e.g., water impermeability and water vapor permeability is desired.

Having described the preferred embodiments, the following examples are presented, but the invention is not limited to be limited thereto.

EXAMPLE 1

High Moisture Vapor Transmission Rate Polymer Using Polyurethaneurea as the Base Polymer Materials Five solutions of A, a low durometer polyurethaneurea based on diphenylmethane diisocyanate (MDI), ethylene diamine (ED) and polytetramethylene oxide (PTMO) were prepared in dimethylacetamide (DMAC). Modifying agents were added to the urethane solution based on the weight of the urethane polymer, resulting in the following solutions:

(a) A
(b) A with 0.5% polysiloxane (I)
(c) A with 0.5% polysiloxane (II)
(d) A with 0.5 Lithium Bromide
(e) A with 0.5 polysiloxane (I) and 0.5% lithium bromide Copolymer (I) consists of a urethane hard block and silicone and polyethylene oxide soft blocks. Copolymer I contains 28% polysiloxane by weight which equates to adding 1.78% of the copolymer in A to yield a 0.5% polysiloxane concentration. Copolymer II consists of urethane and siloxane blocks only. II contains 50% silicone which equates to adding 1.0% of the copolymer to A to yield a 0.5% by weight silicone concentration. Lithium bromide is a salt which increases the polarity and solvent strength of DMAC.

Films ranging in thickness from 0.5 mil to 2.0 mil in increments of 0.5 mil were cast from solution onto release paper by the knife over roll technique. A Talboys web coater was used in the film casting procedure which was equipped with a four foot convection oven maintained at 75±5° C.

The fully cured cast films were removed from the release paper. A micrometer accurate to ±0.0005 inch was employed to measure the thickness of the films.

Fisher/Payne Permeability cups were used to determine the moisture vapor transmission rate (MVTR) of the test specimens. Ten milliliters of distilled water was dispensed into the flanged cup. A disk of the sample was placed over the cup flange followed by a butyl rubber sealing gasket and a metal flat ring. The sample, gasket and ring were secured to the cup flange with three clamps with sufficient pressure to insure a tight seal.

The MVTR of the unsupported cast films were determined by the standard test conditions of ASTM E-96, procedure BW. This procedure involved testing the material at 23±1° C. and 50±2% relative humdity. The cup was inverted allowing the distilled water to cover the inner surface of the film. Air was continuously circulated over the face of the inverted cup at 500 ft/min.

The samples were conditioned for 24 hours at 23° C. and 50% RH prior to testing. The MVTR of five specimens from each cast film were measured. The assembled cups were placed in the test chambers for one hour. The temperature, air velocity and relative humidity were recorded. At the end of this time period, each cup was accurately weighed to 0.1 mg. The cups were inverted and returned to the test chamber for two hours and reweighed. The MVTR of each cup was calculated from equation (1).

$$MVTR = (g)(24\ hr)/(t)(A)$$

where:
g = weight change during test (grams)
t = time of analysis (hour)
A = test area (cup mouth area) (m$^2$)

Each film was analyzed on three separate days to determine the reproducibility of the coating and testing methods.

The means and standard deviation (N=5) of the MVTR of each solvent cast film are contained in Table 1.

TABLE 1

MVTR* OF UNSUPPORTED CAST FILM

MVTR (g/m$^2$/24 hr.)

| Sample/Thickness (nom) | Test 1 $\bar{x} \pm \sigma$ | Test 2 $\bar{x} \pm \sigma$ | Test 3 (N = 5) $\bar{x} \pm \sigma$ |
|---|---|---|---|
| Polyurethaneurea (A) | | | |
| 0.5 mil | 3555 ± 254 | 2964 ± 217 | 3844 ± 356 |
| 1.0 mil | 2282 ± 198 | 1925 ± 84 | 2348 ± 321 |
| 1.5 mil | 1535 ± 94 | 1378 ± 138 | 1303 ± 59 |
| 2.5 mil | 1210 ± 83 | 1355 ± 312 | 1143 ± 123 |
| A w/0.5% Siloxane (I) | | | |
| 0.5 mil | 5063 ± 116 | 4198 ± 384 | 5581 ± 346 |
| 1.0 mil | 2641 ± 163 | 2015 ± 179 | 2210 ± 184 |
| 1.5 mil | 1312 ± 103 | 1188 ± 54 | 1707 ± 128 |
| 2.0 mil | 1455 ± 78 | 1086 ± 126 | 2498 ± 373 |
| A w/0.5% Siloxane (II) | | | |
| 0.5 mil | 3018 ± 154 | 3315 ± 246 | 3704 ± 497 |
| 1.0 mil | 1925 ± 291 | 2598 ± 159 | 2268 ± 127 |
| 1.5 mil | 1144 ± 119 | 1357 ± 673 | 1478 ± 53 |
| 2.0 mil | 1358 ± 83 | 1204 ± 137 | 1105 ± 90 |
| A w/0.5% Lithium Bromide | | | |
| 0.5 mil | 4517 ± 90 | 4622 ± 979 | 4478 ± 447 |
| 1.0 mil | 2838 ± 295 | 2436 ± 295 | 2883 ± 234 |
| 1.5 mil | 1765 ± 88 | 2040 ± 224 | 3073 ± 647 |
| 2.0 mil | 1052 ± 71 | 1459 ± 114 | 1410 ± 60 |
| A w/0.5% Siloxane (I) and 0.5% Lithium Bromide | | | |
| 0.5 mil | 5703 ± 560 | | |
| 1.0 mil | 4034 ± 608 | | |
| 1.5 mil | 1642 ± 160 | | |
| 2.0 mil | | | |

*MVTR = Moisture Vapor Transmission Rate

This data was reduced further as shown on Table 2, by computing the mean and standard deviation of the MVTR and thickness measurements determined on three separate days (N=15).

TABLE 2

MVTR OF UNSUPPORTED CAST FILM

| Mean Sample/Thickness (measured) | MVTR (g/m$^2$/24 hr) (N = 15) |
|---|---|
| Polyurethaneurea (A) | |
| 0.6 mil | 3454 ± 449 |
| 0.97 mil | 2185 ± 227 |
| 1.5 mil | 1405 ± 118 |
| 2.0 mil | 1236 ± 108 |
| A w/0.5% Siloxane (I) | |
| 0.5 mil | 4947 ± 699 |
| 0.93 mil | 2289 ± 320 |
| 1.43 mil | 1402 ± 271 |
| 2.0 mil | 1271 ± 261 |
| A w/0.5% Siloxane (II) | |
| 0.5 mil | 3346 ± 344 |
| 0.97 mil | 2261 ± 332 |
| 1.5 mil | 1326 ± 169 |
| 2.0 mil | 1222 ± 128 |
| A w/0.5% Lithium Bromide | |
| 0.5 mil | 4539 ± 74 |
| 0.93 mil | 2719 ± 246 |
| 1.35 mil | 1903 ± 194 |
| 2.0 mil | 1305 ± 220 |
| A w/0.5% Siloxane (I) and 0.5% Lithium Bromide (N = 5) | |
| 0.5 mil | 5703 ± 560 |
| 1.0 mil | 4034 ± 608 |
| 1.5 mil | 1642 ± 160 |
| 2.0 mil | |

Figure 1:
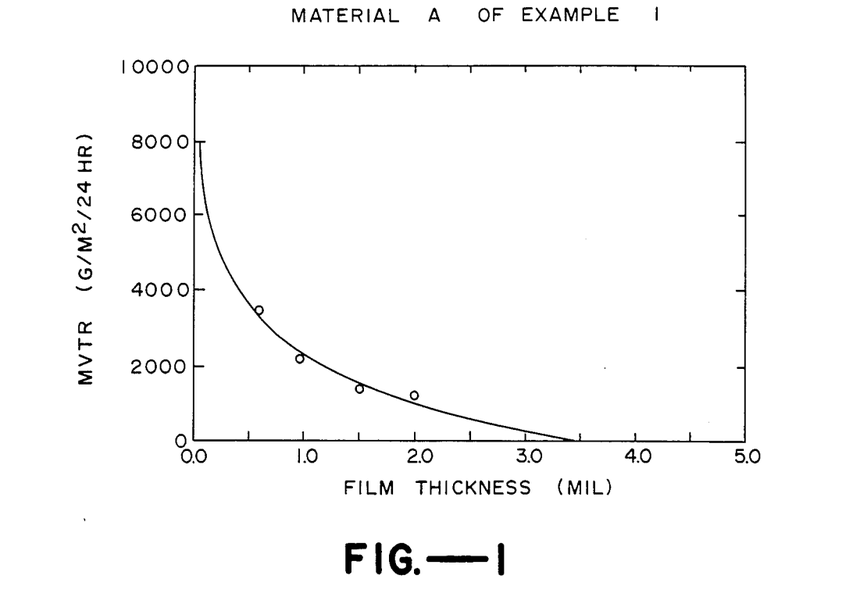
FIG. 1 is a plot of moisture vapor transmission rate vs. film thickness of Material A described in Example 1.
Figure 2:
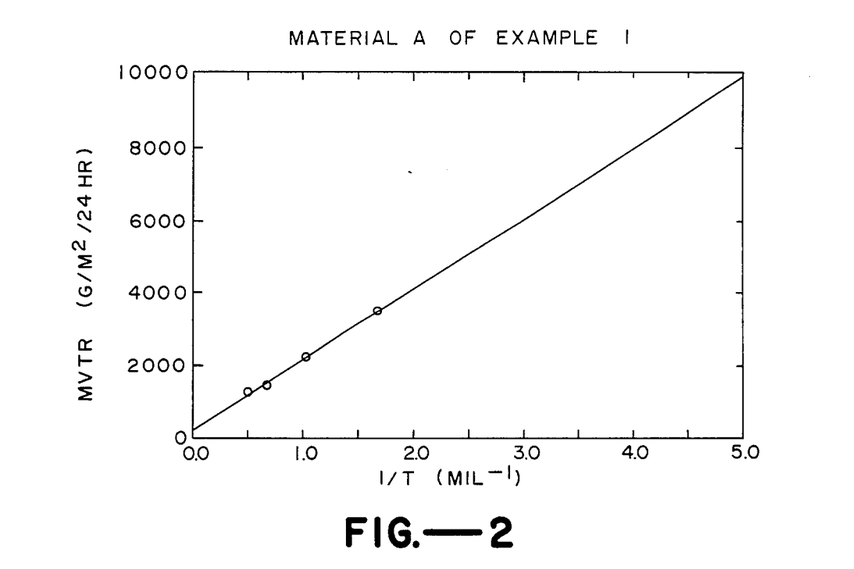
FIG. 2 is a plot of moisture vapor transmission rate vs. reciprocal film thickness of Material A described in Example 1.
Figure 3:
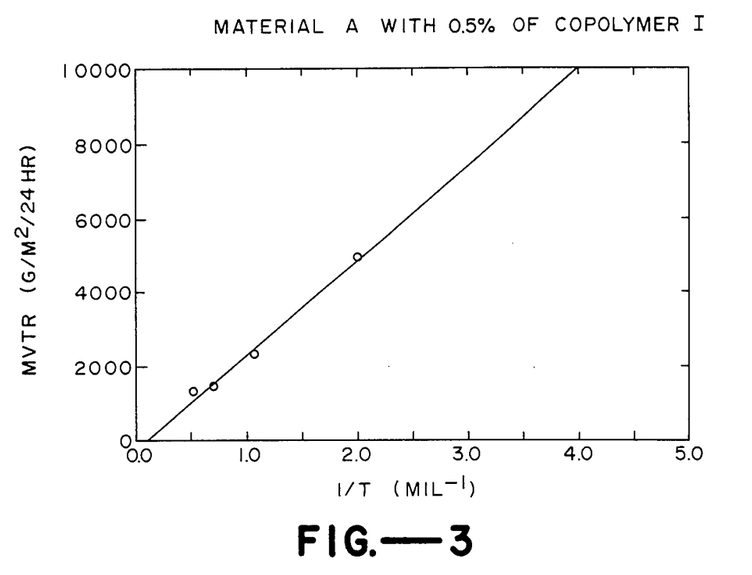
FIG. 3 is a plot of moisture vapor transmission rate vs. reciprocal film thickness of Material A containing 0.5% by weight of siloxane copolymer additive I described in Example 1.
Figure 4:
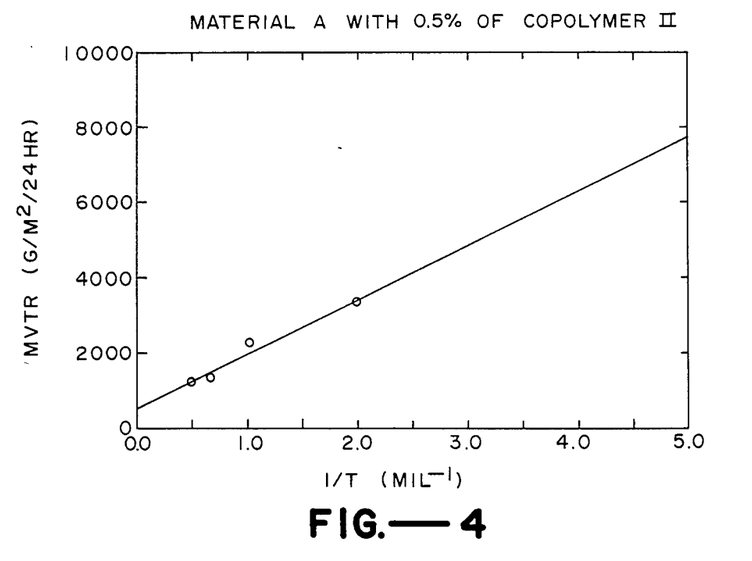
FIG. 4 is a plot of moisture vaor transmission rate vs. reciprocal film thickness of Material A containing 0.5% of siloxane copolymer additive II described in Example 1.
Figure 5:
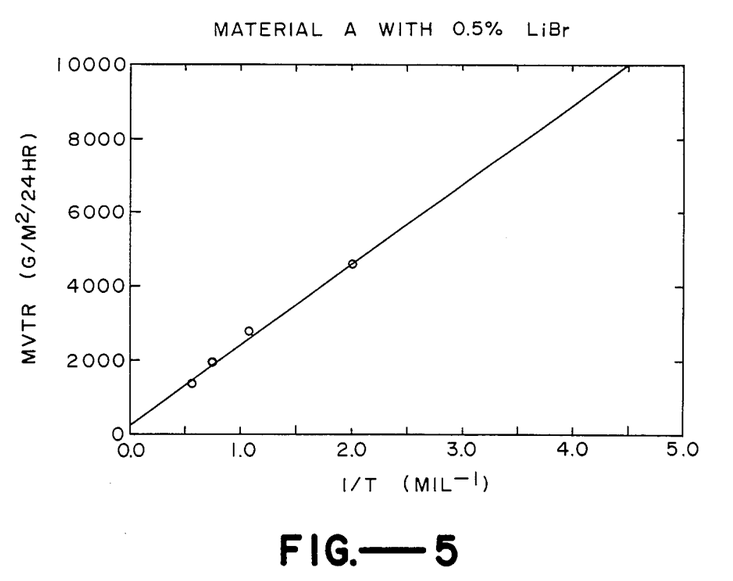
FIG. 5 is a plot of moisture vapor transmission rate vs. reciprocal film thickness of Material A containing 0.5% by weight LiBr.
Figure 6:
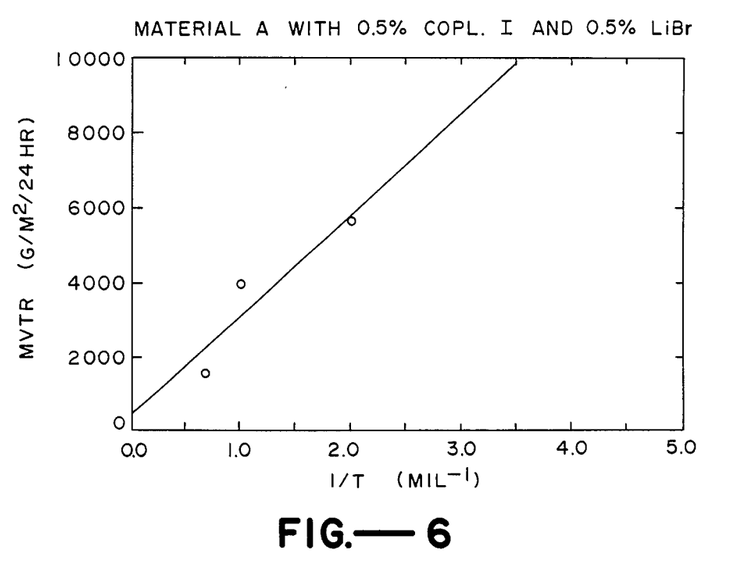
FIG. 6 is a plot of moisture vapor transmission rate vs. reciprocal film thickness of Material A containing 0.5% by weight siloxane copolymer I and 0.5% LiBr.

The data was represented graphically by plotting MVTR as a function of film thickness, FIG. 1. Regression analysis yielded a power curve with the best fit. An alternate method of analyzing the data is to plot MVTR as a function of reciprocal film thickness resulting in a linear relationship between the two variables (FIGS. 2–6). The slope of the linear regression line with the best fit is the permeability coefficient, an important quantity for predicting the theoretical value of the MVTR at a given thickness. Analytically, the slope of a line can be calculated by dividing the y-displacement by the x-displacement or in this case by dividing the MVTR by the reciprocal film thickness. As this number becomes increasingly large, it means that a small reduction in the film thickness will result in a greater increase in the MVTR. Table 3 contains the slope of the linear regression line and the MVTR value of a 0.5 mil film calculated from the slope and the y-intercept of the regression analysis.

TABLE 3

SLOPE OF LINEAR REGRESSION LINE AND CALCULATED MVTR OF 0.5 MIL FILM

| Sample | Slope g mil/m$^2$/24 hr | MVTR (g/m$^2$/24 hr) |
|---|---|---|
| A | 1948 | 4081 |
| A w/0.5% Siloxane (I) | 2575 | 4866 |
| A w/0.5% Siloxane (II) | 1450 | 3416 |
| A w/0.5% LiBr | 2185 | 4598 |
| A w/0.5% Siloxane (I) and 0.5% LiBr | 2731 | 5914 |

It is evident from Table 3 that as the value of the slope increases, the interpolated MVTR value at a 0.5 mil film thickness also increases. The textile coatings and wound dressing films require a large moisture vapor transmission rate for optimum confort during use. The results indicate the following:

Copolymer I increased the 0.5 mil MVTR of the base material by 20%. The combination of I and lithium bromide added to the polyurethaneurea A resulted in an enhancement of the MVTR by 45% when compared to the unmodified A, whereas polyurethane A alone enhanced MVTR by 19% and LiBr alone enhanced MVTR by 13% compared to unmodified polymer. Thus, there appears to be synergy between the Copolymer I and the lithium bromide in enhancing MVTR. Copolymer II which contained no hydrophilic polyethylene oxide block actually reduced MVTR when added to A illustrating the necessary hydrophilic/hydrophobic structure of the additive for MVTR enhancement. Permeability through nonporous films is the product of the diffusivity of the permeant annd its solubility in the film material. Permeability will be increased if either diffusivity or solubility is increased as long as the second quantity is not reduced in the process.

The ability of the additives according to the present invention are believed to enhance the moisture permeability (i.e., MVTR) is due to the fact that they increase both solubility *and* diffusivity of water in the polymer to which they are added. The silicone component in the copolymers of Example 1 (additives I and II) is responsible for enhancing diffusivity. Silicone with its low glass transition temperature, $-130°$ C., and unusually flexible backbone chain has the highest diffusivity to gases and vapors of any common polymer. On the other hand, it is hydrophobic or water repelling and can actually reduce water solubility of blends with itself and the base polymer by an amount which more than compensates for the gain in diffusivity. Thus, when polymer additive II is added to the polyurethanurea, the net effect is a decrease in MVTR. Polymer additive I contains both silicone (hydrophobic) and polyethylene oxide (hydrophilic) blocks. Polyethylene oxide homopolymer is extremely water soluble. Its presence in the base polymer appears to enhance water solubility more than the silicone.

EXAMPLE 2

Preparation of High Moisture Vapor Transmission Rate Films Using Polyesterurethane, Polyetherurethane and Segmented Polyurethaneurea as Base Polymers A 0.5 mil thick film of Estane 5707 (B. F. Goodrich), a polyester urethane, was produced by casting on the web coater using Mylar as the substrate. The moisture vapor transmission rate of this film was 1482 g/m$^2$ for 24 hours with the standard deviation of 118. The same film containing 0.5% silicone in the form of a copolymer containing MDI and butanediol as hard segment and polydimethylsiloxane and polytetramethyleneoxide as the soft segment (II) gave a moisture vapor transmission rate of 2173±157 g/m$^2$. This is a 46.6% increase in moisture vapor transmission rate by adding about 1 to 1½% of the terpolymer, which corresponds to about ½% addition of silicone.

It can be assumed from the MVTR Measurement on pure silica-free silicone that MVTR is 25,128 g/m$^2$ for 24 hours with the silicone component. This can be used to calculate the weighted average between the Estane 5707 and the silicone blend. From this calculation it would be expected that the MVTR would be only 1600 g/m$^2$ for 24 hours. The difference between 1600 and 2173 is 38.6% unexpected increase in MVTR caused by the addition of the silicone in the form of a block copolymer.

The result of the hydrophobic/hydrophilic, or so-called amphiphilic or amphipathic, structure of additive II is apparently that both terms of the permeability are increased simultaneously. That is when additions of type II are combined with a base polymer they increase the diffusivity of water through that base polymer and the solubility of water in that base polymer. Consequently, the product of these two quantities, the permeability, is also increased significantly.

In the second example, Estane 5714 is used which is a polyetherurethane based on PTMO, butanediol and MDI. For a 0.5 mil film of the pure material, an MVTR of 3097±214 g/m$^2$ for 24 hours was obtained. The same Estane 5714 cast in a 0.5 mil thickness but this time containing 0.5% silicone in the form of silicone/PEOM-DI/butanediol terpolymer (I) gave an MVTR of 4895±475 g/m$^2$ for 24 hours. That was an overall increase of 59% relative to the unmodified Estane 5714. Again using the weighted average approach, it would be expected that MVTR for the blend would be only 3289 g/m$^2$ for 24 hours. Therefore, a 1606 g/m$^2$/24 hour increase in MVTR was obtained or an unexpected 48.8% increase relative to what would be expected from the weighted average.

In a third example Biomer ®, a segmented polyurethaneurea, was used. A 0.5 mil thick sheet of this material gave MVTR of 3170±243 g/m$^2$ whereas the same material with 0.5% silicone in the form of the terpolymer (I) used in the above two examples gave 3963±160 g/m$^2$ for 24 hours with an MVTR of 25% increase over the unmodified Biomer. The weighted average or expected value would be 3295 g/m$^2$ for 24 hours. This represents a 20.3% unexpected increase in MVTR as caused by the additive.

EXAMPLE 3

Preparation of High Moisture Vapor Transmission Films Utilizing Polyether Polyester Elastomer as Base Polymer Methylene chloride may be used to dissolve 40D Hytrel material (DuPont) but, because of its marginal solubility, cannot be prepared in a solid content above about 11%. The resulting dilute solution, which is stable at ~10% solids, has a viscosity which is too low to be handled easily in film preparation. By combining Cab-O-sil fumed silica with the methylene chloride solution, proper viscosity may be achieved. Because the solvent based Hytrel solution is relatively nonpolar, the "Cab-O-Sil" material is not an optimally effective thickener. Low molecular weight polyethylene glycols are innocuous, nontoxic materials which are polar and water soluble. Their addition to the above described solution serves to enhance the thickening action of the "Cab-O-Sil". Because they are water soluble, they can be removed in an aqueous environment rendering the film more porous than it would have been in the absence of such an additive.

The same burn wound dressing material with silicone-containing block copolymer additives according to Example 1 (i.e. additive I) was prepared with polyethyleneglycol and may be useful in burn wound applications where adhesion to the wound has to be minimized. Also, the film is characterized by a smooth and slippery feel which is desirable in dressing applications.

EXAMPLE 4

Preparation of High Vapor Transmission Films Containing Siloxane without a Base Polymer A reactor is charged under nitrogen with 35 g (0.0244 moles) polyethylene oxide, 100 g (0.0492 moles) polytetramethylene oxide, 1.5 g (0.0006 moles) polydimethysiloxane/polyethylene oxide block copolymer, 320 ml. dimethylformamide and is heated to 45° C. Then 26.0 g (0.1040 moles) para, para'-diphenyl-methane diisocyanate is added and the mixture is maintained at 45±3° C. with agitation for 3 hrs. Heating is halted and the reactor is charged with 0.66 ml. (0.009 moles) ethylene diamine followed immediately by 355 ml. dimethylformamide, taking caution to control the exotherm below 50° C. At approximately 10 minute intervals, the remainder of the ethylene diamine is added according to the following schedule:

| | |
|---|---|
| 1st addition (described above): | 0.66 ml. |
| 2nd addition: | 0.66 ml. |
| 3rd addition: | 0.33 ml. |
| 4th addition: | 0.33 ml. |
| Total | 1.98 ml. (0.0297 moles) |

The reaction mixture is stirred for approximately one hour after the final additiona. A film-forming, thermoplastic material is yielded with the following properties: MVTR=15,283 g/m$^2$/24 hr. for a 0.5 mil film. Young's modulus=610±38 PSI, tensile strength=4514 PSI, ultimate elongation=1085.

EXAMPLE 5

Preparation of High Vapor Transmission Films Containing Siloxane without a Base Polymer A reactor is charged under nitrogen with 58.0 g (0.0405 moles) polyethylene oxide, 71.0 g (0.0349 moles) polytetramethylene oxide, 1.7 g (0.0007 moles) of a polydimethylsiloxane/polyethylene oxide block copolymer, and 250 ml. dimethylformamide, heated to 45±3° C. Add 31.8 g (0.1272 moles), para, para'-diphenylmethane diisocyanate and maintained at 45° C. with agitation for 3 hrs. Then 350 ml. dimethylformamide is added, followed by a solution of 3.42 ml. ethylene diamine dissolved in 100 ml. dimethyformamide gradually added over approximately a one-half hr. period. The reaction temperature is maintained to less than 50° C. throughout the addition of chain extender. Following chain extension, the solution is stirred for an additional hour. This yields a film-forming material with the following properties: MVTR=36,243 g/m$^2$/24 hr. for 0.5 ml film. Young's modulus=1194±95 PSI, tensile strength=3156±176 PSI, ultimate elongation (%)=1046±59. Young's modulus of a wet film (24 hrs. water immersion)=858±50 PSI, tensile strength of a wet film=2484±97 PSI, ultimate elongation (%)=1204±63.

EXAMPLE 6

Preparation of High Vapor Transmission Films without Siloxane and without a Base Polymer A nitrogen-purged reactor is charged with 57.9 g (0.0404 moles) polyethylene oxide, 72.8 g (0.0358 moles) polytetramethylene oxide, and 250 ml dimethylformamide and the temperature is raised to 45±3° C. Then 31.8 g (0.1272 moles) para, para'-diphenylmethane diisocyanate is added and the mixture is agitated for 3 hours at 45° C.

Then 350 ml additional dimethylformamide is added followed by gradual addition of a solution of 3.07 g (0.0510 moles) ethylene diamine in 100 ml dimethylformamide over a one-half hour period. The solution temperature is maintained to less than 50° C. throughout the reaction of the chain extender.

Following complete addition of the chain extender, the mixture is agitated for an additional hour. This yields a film-forming material with the following properties:
MVTR=21,738 g/m$^2$—24 hours for a 0.5 mil film
Young's Modulus=998±67 psi
Tensile Strength=0.3414±228 psi
Ultimate Elongation (5)=937±30
Young's Modulus of a wet film (24 hours water immersion)=854±60 psi
Tensile Strength of a wet film=3232±105 psi
Ultimate Elongation (%) of a wet film=1156±89

EXAMPLE 7

Preparation of High Vapor Transmission Films Containing Siloxane without a Base Polymer A reactor under nitrogen atmosphere is charged with 39.7 g (0.0277 moles) polyethylene oxide, 38.2 g (0.0188 moles) polytetramethylene oxide, 1.6 g (0.0007 moles) of a polydimethylsiloxane/polyethylene oxide block copolymer, and 61.5 g (0.2458 moles) para, para'-diphenylmethane diisocyanate and 200 ml dimethylformamide, then heated to 42±3° C. The temperature is maintained with agitation for 3 hours, then diluted with 60 additional ml dimethylformamide.

Then 17.9 g (0.1987 moles) 1,4-butanediol in 75 ml dimethylformamide is placed into an additional funnel and approximately ¾ of this butanediol solution is added to the reaction mixture. After one hour, the remainder of the solution is added and the mixture is allowed to react for 2 additional hours. A film-forming material was yielded possessing the following characteristics:
MVTR=7618 g/m$^2$—24 hours for a 0.5 mil film thickness
Young's Modulus=3915±257 psi
Tensile Strength=4388 psi
Ultimate Elongation (%)=729±31
Young's Modulus of a wet film (24 hours water immersion)=3767±128 psi
Tensile Strength of a wet film=3592±151 psi
Ultimate Elongation (%) of a wet film=756±37

What is claimed is:

1. A coated textile impermeable to liquid water characterized by high moixture vapor transmission comprising a fabric web and a uniform nonporous coating on at least one surface of said web, said coating comprising a segmented block multipolymer comprising an essentially linear segmented copolymer chain characterized by at least one polyurethane or polyurethane urea hard segment and a soft block copolymer comprising at least one hydrophilic soft block and at least one hydrophobic soft block.

2. A textile according to claim 1 wherein said hard segment is a homopolymer selected from the group consisting of condensation products of diphenylmethane diisocyanate with a diamine and diphenylmethane diisocyanate with a diol.

3. A textile according to claim 2 wherein said hydrophilic soft block comprises polyethylene oxide and said hydrophobic soft block comprises polytetraalkylene oxide.

4. A textile according to claim 3 wherein said soft block copolymer further comprises a polydialkylsiloxane hydrophobic soft block.

5. A textile according to claim 3 wherein said coating comprises:

| | |
|---|---|
| 15–50% | by weight of said hard segment |
| 20–45% | polyethylene oxide (1000–3000 mol. wt (number average)) |
| 25–65% | polytetramethylene oxide |
| 100% | |

6. A textile according to claim 5 wherein said coating further comprises up to 2% by weight polydimethylsiloxane.

* * * * *